United States Patent
Hale et al.

(10) Patent No.: US 10,675,485 B2
(45) Date of Patent: Jun. 9, 2020

(54) RADIATION DOSAGE MONITORING SYSTEM

(71) Applicant: Vision RT Limited, London (GB)

(72) Inventors: Gideon Matthew Hale, London (GB); Ivan Daniel Meir, London (GB); Todd Pawlicki, San Diego, CA (US); Martin Allen, London (GB)

(73) Assignee: Vision RT Limited, London (GB)

( * ) Notice: Subject to any disclaimer, the term of this patent is extended or adjusted under 35 U.S.C. 154(b) by 231 days.

(21) Appl. No.: 15/647,160

(22) Filed: Jul. 11, 2017

(65) Prior Publication Data
US 2017/0304653 A1    Oct. 26, 2017

Related U.S. Application Data

(62) Division of application No. 15/089,494, filed on Apr. 2, 2016, now Pat. No. 9,731,150.

(30) Foreign Application Priority Data

May 12, 2015 (GB) .................... 1508104.5
Mar. 31, 2016 (GB) .................... 1605424.9

(51) Int. Cl.
*A61N 5/10* (2006.01)
*H04N 13/246* (2018.01)
(Continued)

(52) U.S. Cl.
CPC .......... *A61N 5/1071* (2013.01); *A61B 5/0071* (2013.01); *A61N 5/1048* (2013.01);
(Continued)

(58) Field of Classification Search
CPC .................................................. A61N 5/1071
See application file for complete search history.

(56) References Cited

U.S. PATENT DOCUMENTS

| 7,348,974 | B2 | 3/2008 | Smith et al. |
| 7,889,906 | B2 | 2/2011 | Smith et al. |

(Continued)

FOREIGN PATENT DOCUMENTS

| GB | 2530790 A | 4/2016 |
| GB | 2532077 A | 5/2016 |

(Continued)

OTHER PUBLICATIONS

Sep. 23, 2015 Combined Search and Examination Report issued in British Patent Application No. 1508104.5.
(Continued)

*Primary Examiner* — Rowina J Cattungal
(74) *Attorney, Agent, or Firm* — Birch, Stewart, Kolasch & Birch, LLP

(57) ABSTRACT

A radiation dosage monitoring system comprising a 3D camera operable to obtain images of a patient undergoing radiation treatment, the 3D camera being operable to detect Cherenkov radiation and any subsequent secondary and scattered radiation originating due the initial Cherenkov radiation emitted from a surface of the patient when the patient is irradiated by a radiation beam; and a processing module operable to process the images obtained by the 3D camera utilizing data indicative of chromophores present in a patient's skin to apply a correction factor to such images to account for absorption of Cherenkov radiation by chromophores in the skin when utilizing the images to generate a representation of radiation applied to the surface of the patient.

10 Claims, 3 Drawing Sheets

(51) Int. Cl.
*G01T 1/29* (2006.01)
*G06T 7/80* (2017.01)
*A61B 5/00* (2006.01)
*G01T 1/22* (2006.01)
*G06T 7/00* (2017.01)
*G06T 15/04* (2011.01)

(52) U.S. Cl.
CPC .............. *A61N 5/1075* (2013.01); *G01T 1/22* (2013.01); *G01T 1/29* (2013.01); *G06T 7/0012* (2013.01); *G06T 7/85* (2017.01); *G06T 15/04* (2013.01); *H04N 13/246* (2018.05); *A61N 2005/1059* (2013.01); *A61N 2005/1072* (2013.01); *A61N 2005/1085* (2013.01); *G06T 2200/04* (2013.01); *G06T 2207/30244* (2013.01)

(56) References Cited

U.S. PATENT DOCUMENTS

| | | |
|---|---|---|
| 8,135,201 B2 | 3/2012 | Smith et al. |
| 2006/0079757 A1* | 4/2006 | Smith ................. A61N 5/1049 600/416 |
| 2008/0319283 A1 | 12/2008 | Cotton et al. |
| 2009/0080726 A1 | 3/2009 | Cotton et al. |
| 2009/0187112 A1 | 7/2009 | Meir et al. |
| 2013/0188856 A1* | 7/2013 | Adler, Jr. ................. A61B 6/12 382/132 |
| 2014/0114150 A1* | 4/2014 | Pogue ................. A61N 5/1075 600/317 |

FOREIGN PATENT DOCUMENTS

| | | |
|---|---|---|
| WO | 2012159043 A2 | 11/2012 |
| WO | 2014057280 A1 | 4/2014 |
| WO | 2015008040 A2 | 1/2015 |
| WO | 2015077480 A1 | 5/2015 |
| WO | WO-2015077480 A1 * | 5/2015 ............... G01T 1/22 |

OTHER PUBLICATIONS

Lutz W, et al; "A system for stereotactic radiosurgery with a linear accelerator" Int J Radiat Oncol Biol Phys. 1988, 14(2):373-81.
Jun. 1, 2016 Search and Examination Report issued in British Patent Application No. GB1508104.5.

* cited by examiner

RADIATION DOSAGE MONITORING SYSTEM

CROSS REFERENCE TO RELATED APPLICATION

This application is a divisional application of U.S. application Ser. No. 15/089,494, filed Apr. 2, 2016 which claims priority to British Application 5 No.: 1508104.5, filed on May 12, 2015, and British Application No.: 1605424.9, filed on Mar. 31, 2016, the contents of which are hereby incorporated in their entireties by reference.

FIELD OF THE INVENTION

The present invention concerns a radiation dosage monitoring system. In particular, embodiments of the present invention concern a radiation dosage monitoring system for monitoring radiation dosages applied to a patient undergoing radiation treatment.

BACKGROUND TO THE INVENTION

Radiotherapy consists of projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful. If movement of a patient is detected during treatment, the treatment should be halted to avoid irradiating areas of a patient other than a tumour location.

For this reason a number of monitoring systems for assisting the positioning of patients during radiotherapy and detecting patient movement have therefore been proposed such as those described in Vision RT's earlier patents and patent applications U.S. Pat. Nos. 7,889,906, 7,348,974, 8,135,201, US2009/187112, WO2014/057280, and WO2015/008040.

In the systems described in Vision RT's patent applications, stereoscopic images of a patient are obtained and processed to generate data identifying 3D positions of a large number of points corresponding to points on the surface of an imaged patient. Such data can be compared with data generated on a previous occasion and used to position a patient in a consistent manner or provide a warning when a patient moves out of position. Typically such a comparison involves undertaking Procrustes analysis to determine a transformation which minimises the differences in position between points on the surface of a patient identified by data generated based on live images and points on the surface of a patient identified by data generated on a previous occasion.

Treatment plans for the application of radiotherapy are becoming increasingly complex with treatment apparatus having multiple or floating iso-centres. Also, there is an increasing trend to make use of higher doses of radiation during treatment in order to reduce overall treatment time. Such increasing complexity and higher dosages bring with them the increasing possibility of mistreatment. With the increasingly complex treatment plans, in addition to identifying the location and dosage of radiation at the surface of the patient, it would be desirable to identify the internal locations where radiation is applied and to obtain feedback on the radiation dosages applied internally during the course of treatment.

Another problem associated with monitoring patients during radiotherapy treatments is the fact that the appearance of the Cherenkov radiation emitted from a patient undergoing radiotherapy is dependent on the skin tone or colour, more specifically, on the level of chromophores present in the skin of the patient. The two chromophores which are of greatest significance are blood and melanin. This has the effect that any estimate of radiation received by the patient could be either too high or too low if the level of chromophores in the skin is not taken into account when determining that estimate. It will be understood that an incorrect estimation of the levels of radiation received by the patient estimate can have serious consequences to the well being of the patient as it is the estimates which are used to determine compliance with a radiation treatment plan which has been calculated to deliver the correct levels of radiation to the patient. Too low an estimate will result in increased levels of radiation being applied to comply with the treatment plan and lead to possible damage to the patient's tissue. Conversely, too low an estimate will result in not enough radiation being applied to the patient and lead to incomplete irradiation of the tumour being treated. This is particularly important as it has already been stated above that there is an increasing trend to make use of higher doses of radiation during treatment in order to reduce overall treatment time, with such higher dosages bringing with them the increasing possibility of mistreatment.

SUMMARY OF THE INVENTION

In accordance with one aspect of the present invention there is provided a radiation dosage monitoring system comprising a 3D camera operable to obtain images of a patient undergoing radiation treatment, the 3D camera being operable to detect Cherenkov radiation and any subsequent secondary and scattered radiation originating due the initial Cherenkov radiation emitted from a surface of the patient when the patient is irradiated by a radiation beam, and a processing module operable to process the images obtained by the 3D camera utilizing data indicative of chromophores present in a patient's skin to apply a correction factor to such images to account for absorption of Cherenkov radiation by chromophores in the skin when utilizing the images to generate a representation of radiation applied to the surface of the patient.

In such an embodiment the processing module may be arranged to convert images into images representative of radiation skin dosage by modifying pixel values in accordance with a correction factor to account of the absorption of Cherenkov radiation and any subsequent secondary and scattered radiation originating due the initial Cherenkov radiation by chromophores present in a patient's skin.

In some embodiments the processing module may be operable to process images obtained by the image detector to determine data indicative of chromophores present in a patient's skin and the correction factor applied is determined on the basis of said data. Alternatively, data indicative of chromophores present in a patient's skin may comprise a visual estimation of the skin colour of the patient based on a comparison with a reference set of skin tones and the correction factor applied is determined on the basis of said data.

The radiation dosage monitoring system may form part of a radiotherapy treatment system arranged to inhibit the irradiation of a patient if the estimations of radiation dosages received by the modelled portion of the surface of the patient determined by the radiation dosage monitoring system differ from a predetermined estimations of radiation dosages of a patient irradiated in accordance with a defined treatment plan by more than a threshold amount. The radiation dosage monitoring system may form part of a radiotherapy treatment system arranged to inhibit the irradiation of a patient if the estimations of radiation dosages received by internal portions of the patient determined by the radiation dosage monitoring system differ from a predetermined 3D internal representation of the location of the portions of a patient irradiated in accordance with a defined treatment plan by more than a threshold amount.

A further aspect of the present invention provides a method of calibrating a stereoscopic camera system for use with a radio therapy treatment apparatus, the method comprising utilizing a radio therapy treatment apparatus to apply radiation to a calibration object when radio therapy treatment apparatus is in a first and in a second orientation; obtaining images of Cherenkov radiation emitted by the calibration object when the radiation is applied; and processing the obtained images to determine the relative position and orientation of the stereoscopic camera relative to a point in space through which the radiation beam passes when in both the first and in the second orientation.

BRIEF DESCRIPTION OF THE DRAWINGS

Embodiments of the present invention will now be described with reference to the accompanying drawings in which:

FIG. 1 is a schematic perspective view of an embodiment of a radiation dosage monitoring system in accordance with an embodiment of the present invention.

DETAILED DESCRIPTION OF THE PREFERRED EMBODIMENTS

Figure 1:
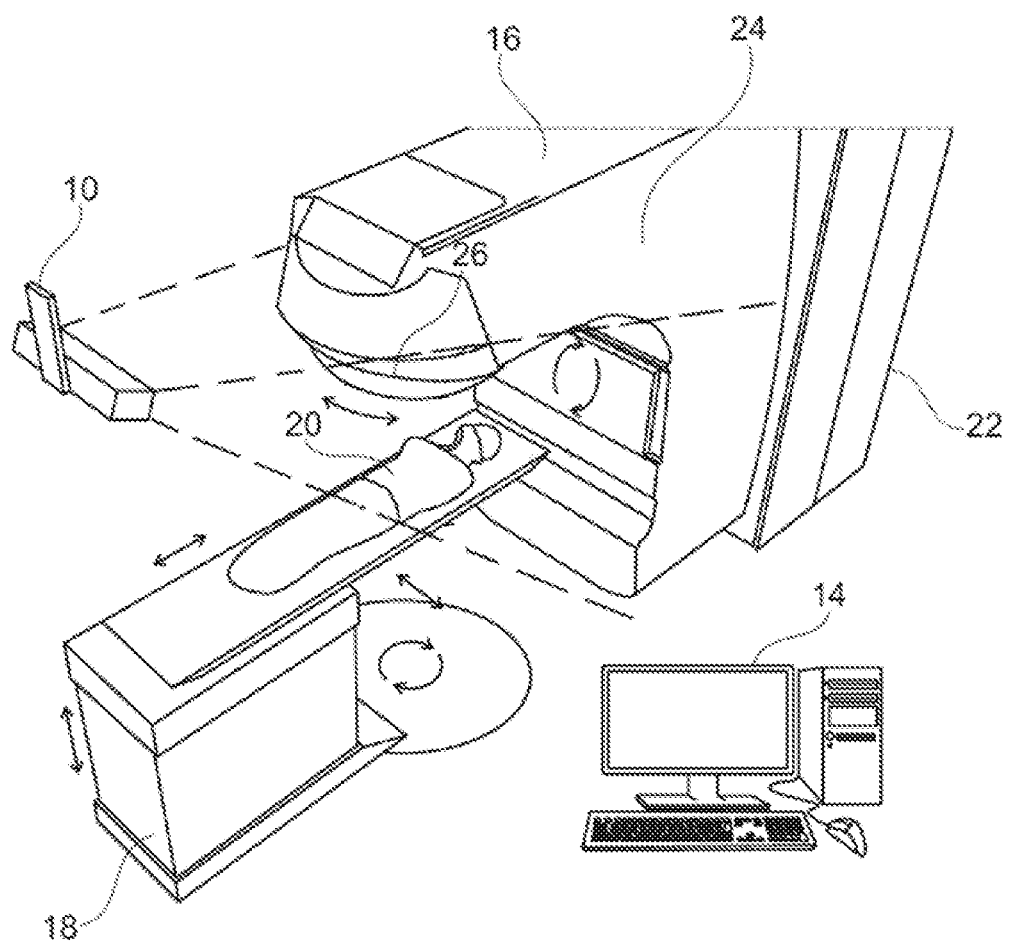
FIG. 1 is a schematic perspective view of a radiation dosage monitoring system in accordance with an embodiment of the present invention.

The radiation dosage monitoring system comprises a stereoscopic camera system 10 that is connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the centre of the main body 22 of the treatment apparatus 16. Additionally the location of irradiation by the treatment apparatus may also be varied by rotating the collimator 26 at the end of the gantry 24.

In use, the stereoscopic camera 10 obtains video images of a patient 20 lying on the mechanical couch 18. These video images are passed via the wiring to the computer 14. The computer 14 then processes the images of the patient 20 to generate a model of the surface of the patient.

As in a conventional patient positioning system, this model can be compared with a model of the patient generated during earlier treatment sessions. When positioning a patient the difference between a current model surface and a target model surface obtained from an earlier session is identified and the positioning instructions necessary to align the surfaces are determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

However, in accordance with the present invention, in addition to obtaining images of a patient and generating a model of the surface of a patient being monitored, in this embodiment, the stereoscopic camera 10 also obtains images of Cherenkov radiation emitted from a patient by virtue of radiation from the treatment apparatus 16 entering the patient's body moving at greater than the effective speed of light of the radiation within irradiated tissue. The projection of the detected Cherenkov radiation on the surface of a patient is compared with the expected pattern of Cherenkov radiation estimated based on a treatment plan and if the detected pattern and expected pattern do not match this may indicate an error in set up and treatment can be halted.

In addition to comparing detected Cherenkov radiation with an expected pattern of Cherenkov radiation, the computer 14 also records the cumulative levels of Cherenkov radiation emitted from portions of a patient being monitored. This can provide an indication of cumulative skin radiation dose.

Finally, in addition to monitoring the surface of the skin, in this embodiment of the present invention, the stereoscopic camera 10 is arranged to monitor the position and orientation of the treatment apparatus 16 to determine the orientation of an emitted radiation beam emitted by the apparatus. This can be achieved by for example monitoring the positions of a number of markers (not shown) on the surface of the treatment apparatus 16. This beam orientation data together with the record of emitted Cherenkov radiation and a computer model of the portion of a patient being irradiated can generate a model of the estimated radiation dosages applied in a course of treatment. This model can then be compared with an expected pattern of dosage which can be utilised to determine or alter future treatment plans.

Figure 2:
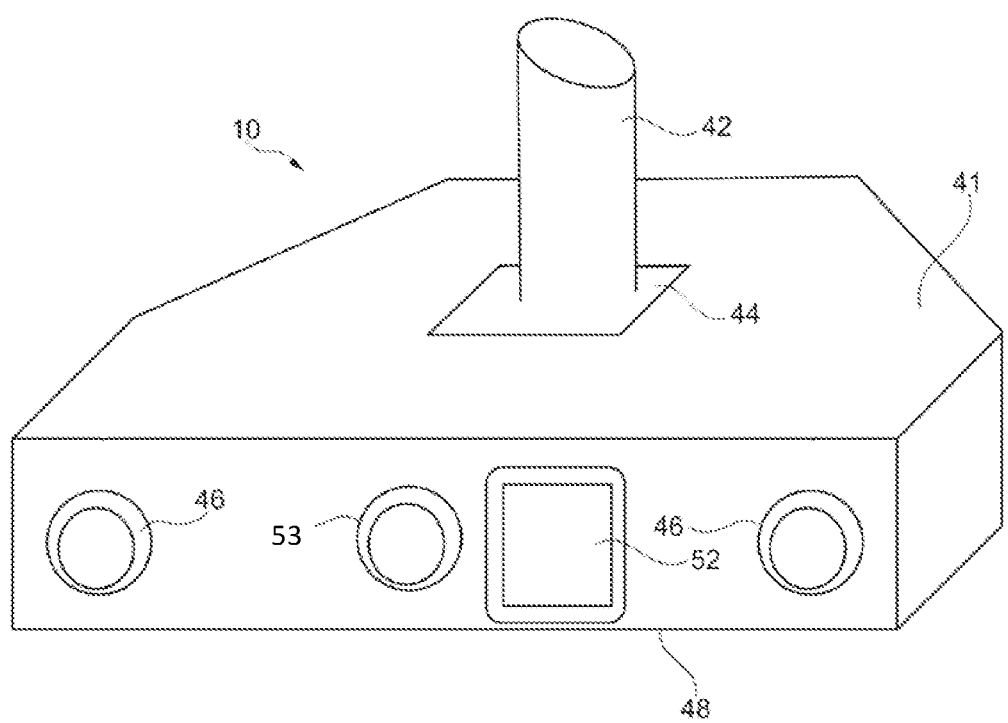
FIG. 2 is a front perspective view of the camera system of the patient monitor of FIG. 1.

FIG. 2 is a front perspective view of a stereoscopic camera system 10 of the radiation dosage monitoring system of FIG. 1.

In this embodiment the stereoscopic camera system 10 comprises a housing 41 which is connected to a bracket 42 via a hinge 44. The bracket 42 enables the stereoscopic camera system 10 to be attached in a fixed location to the ceiling of a treatment room whilst the hinge 44 permits the orientation of the stereoscopic camera system 10 relative to the bracket 42 so that the stereoscopic camera system 10 is arranged to view a patient 20 on a mechanical couch 18.

A pair of lenses 46 is mounted at either end of the front surface 48 of the housing 41. These lenses 46 are positioned in front of image detectors such as CMOS active pixel sensors or charge coupled devices (not shown) contained within the housing 41. The image detectors are arranged behind the lenses 46 so as to capture images of a patient 20 via the lenses 46. In some embodiments the housing 41 may be made of a material such as lead which provides very good shielding from radiation and thereby reduce the extent to which energetic particles generate random errors in images obtained by the image detectors.

A speckle projector 52 is provided in the middle of the front surface 48 of the housing 41 between the two lenses 46. The speckle projector 52 is arranged to illuminate a patient 20 with a pseudo random speckled pattern of infrared light so that when images of a patient 20 are captured by the two image detectors corresponding portions of captured images can be distinguished. To that end the speckle projector comprises a light source such as a LED and a film with a random speckle pattern printed on the film. In use light from the light source is projected via the film and as a result a pattern consisting of light and dark areas is projected onto the surface of a patient 20. When images of the projected speckle pattern are captured by the stereoscopic camera system 10 the images can then be processed to determine the positions of a set of points on the surface of the patient and hence the positioning of the patient can be monitored.

A further lens 53 is provided adjacent the speckle projector 52 which is mounted in front of a further image detector (not shown) contained within the housing 41. This image detector is arranged behind the lens 53 so as to capture images of Cherenkov radiation emitted from the surface of a patient 20 when the patient is irradiated by a radiation beam.

Cherenkov radiation induced when external radiation is applied to tissue is dependent upon a number of factors. Cherenkov light, induced in tissue, is typically predominantly blue in colour, but with a broad spectrum which tapers off into the green, red, and the near infra-red with an inverse square wavelength dependence given by the Frank-Tamm formula. This light emitted in tissue is attenuated by absorbers in the tissue, and can also excite other molecular species in tissue, inducing their photo-luminescence (fluorescence or phosphorescence). The appearance of Cherenkov light will also be influenced by the concentrations of chromophores (principally blood and melanin) in the skin.

Compared with other light sources the levels of Cherenkov radiation induced when irradiating a patient are relatively weak. However, as the timing with which radiation is applied by a treatment apparatus 16 in accordance with a treatment plan is known in advance, the image detector arranged to capture images of emitted Cherenkov radiation can be arranged to be activated for the periods of time when the Cherenkov radiation is expected to be emitted. At the same time external light sources such as room lighting or the speckle projector 52 can be switched off so as to reduce competing sources of light. Since a radiation beam is typically activated many times a second, this switching can potentially be at a speed which is not necessarily detectable by a patient. In some embodiments suitable timing can be achieved by utilising the activation signal for activating the radiation beam as a trigger for activating the image detector and/or deactivating room lighting or the speckle projector 52 with suitable delays so as to ensure that the image detector captures images of a patient when Cherenkov radiation is likely to be induced and external light sources are switched off for the periods of time when the image detector obtains an image.

Figure 3:
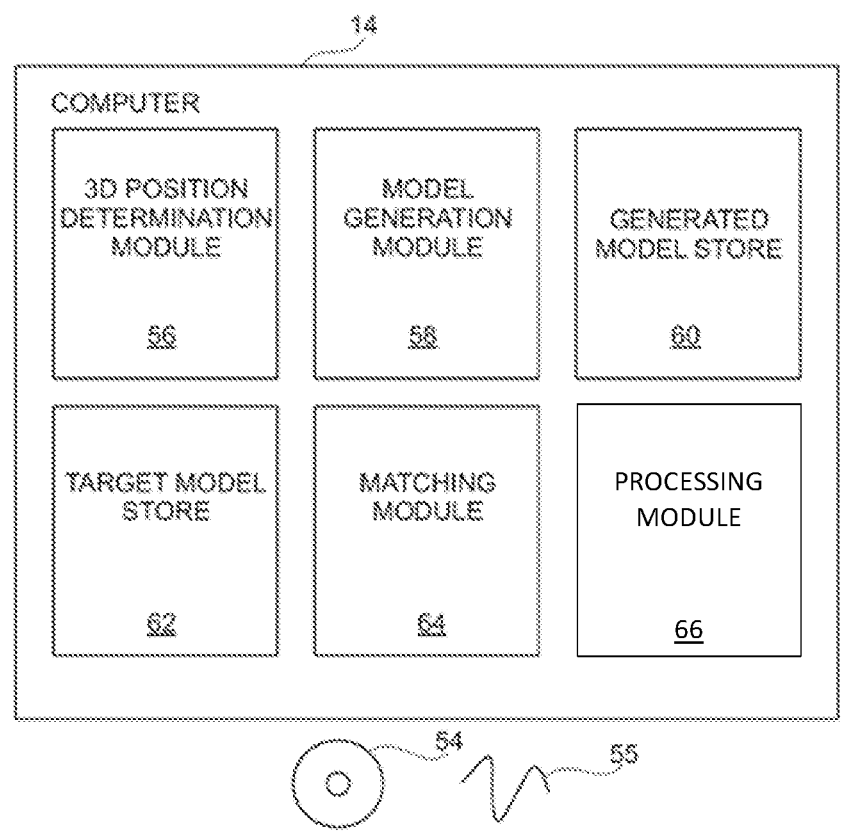
FIG. 3 is a schematic block diagram of the computer system of the patient monitor of FIG. 1.

FIG. 3 is a schematic block diagram of the computer 14 of the patient monitor of FIG. 1.

In order for the computer 14 to process images received from the stereoscopic camera system 10, the computer 14 is configured by software either provided on a disk 54 or by receiving an electrical signal 55 via a communications network into a number of functional modules 56-66. It will be appreciated that the functional modules 56-66 illustrated in FIG. 3 are purely notional in order to assist with the understanding of the working of the claimed invention and may not in certain embodiments directly correspond with blocks of code in the source code for the software. In other embodiments, the functions performed by the illustrated functional modules 56-66 may be divided between different modules or may be performed by the re-use of the same modules for different functions.

In this embodiment, the functional modules 56-66 comprise: a 3D position determination module 56 for processing images received from the stereoscopic camera system 10, a model generation module 58 for processing data generated by the 3D position determination module 56 and converting the data into a 3D wire mesh model of an imaged surface; a generated model store 60 for storing a 3D wire mesh model of an imaged surface; a target model store 62 for storing a previously generated 3D wire mesh model; a matching module 64 for determining rotations and translations required to match a generated model with a target model; and a processing module 66 for processing a generated model and obtained images of Cherenkov radiation to determine estimates of induced radiation and radiation dosages.

In use, as images are obtained by the stereoscopic camera system 10, these images are processed by the 3D position determination module 56. This processing enables the 3D position determination module 56 to identify 3D positions of points on the surface of a patient 20. This is achieved by the 3D position determination module 56 identifying corresponding points in pairs of images obtained by the stereoscopic camera system 10 and then determining 3D positions for those points based on the relative positions of corresponding points in obtained pairs of images and stored data identifying the relative positions of cameras obtaining the images.

Typically the identification of corresponding points is based on analysis of image patches of around 16×16 pixels. In order to assist with identifying and matching corresponding patches as has been described the stereoscopic camera system 10 includes a speckle projector 52 arranged to project a pseudo random speckle pattern onto the patient 20 being imaged so that different portions of the surface of the patient 20 can be more easily distinguished. The size of the speckle pattern is selected so that different patterns will be apparent in different image patches.

The position data generated by the 3D position determination module 56 is then passed to the model generation module 58 which processes the position data to generate a 3D wire mesh model of the surface of a patient 20 imaged by the stereoscopic cameras 10. In this embodiment the 3D model comprises a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the stereoscopic cameras 10 and a previously generated model surface of the patient stored in the target model store 62. The determined translation and rotation can then be sent as instructions to the mechanical couch 18 to cause the couch to position the patient 20 in the same position relative to the treatment apparatus 16 as they were when they were previously treated.

Subsequently, the stereoscopic cameras 10 can continue to monitor the patient 20 and any variation in position can be identified by generating further model surfaces and comparing those generated surfaces with the target model stored in the target model store 62. If it is determined that a patient has moved out of position, the treatment apparatus 16 can be halted and the patient 20 repositioned, thereby avoiding irradiating the wrong parts of the patient 20.

The processing module 66 processes a generated wire mesh model of the surface of a patient and obtained images of Cherenkov radiation obtained by the image detector behind the third lens 53 of the stereoscopic camera 10 to determine the location and position of the emitted radiation.

More specifically, in this embodiment the processing module 66 processes batches of images obtained by the image detector behind the third lens 53. Initially, a first image of the portion of the patient being treated is obtained in the absence of lighting or light projected from the speckle projector 52 and without the patient being irradiated by the treatment apparatus 16. This image is then used as a base reference image for identifying induced Cherenkov radiation.

Subsequent images of the patient are then obtained whilst the patient 20 is irradiated by radiation applied by the treatment apparatus 16.

In addition to monitoring the patient 20, the stereoscopic camera 10 can be arranged to monitor the actual orientation of the gantry 26 and collimator 20 of the treatment apparatus 16 to determine the orientation of a radiation beam at any given time which causes Cherenkov radiation to be emitted. By knowing the orientation of the radiation beam at any time, and the location and position of the emitted radiation at the surface of the patient as described above, it is possible to model the path of the radiation at the surface along the known radiation beam orientation to generate a 3D internal representation of the location of the portions of a patient irradiated.

As an initial step, the obtained images are processed to identify random errors in the images which might be induced by the radiation or other energetic particles emitted during the course of treatment. This is achieved by identifying portions of images corresponding to saturated pixels. If a pixel is saturated (i.e. identifies a completely white pixel) or other pixel value which is a statistical outlier compared with the rest of the image typically this occurs due to an image detector having been struck by an energetic particle and the saturated pixel will not appear as such in a successive image. Thus by identifying pixels corresponding to such random collisions and setting such pixels to the value of such a pixel in the base reference image, random errors due to the random collisions of an energetic particle with the image detector are removed from the obtained data.

A set of difference images is then determined by subtracting the base reference image from each of the other images in the set. This should eliminate from the images any variation in the images relating to background lighting etc. and as the base reference image should be an image in the absence of any Cherenkov radiation, this should mean that the resultant difference images only identify detected emissions of Cherenkov radiation.

The resultant difference images are then utilised to texture render the 3D model surface of the patient being treated.

It will be appreciated that the manner in which the differences images are utilised to texture render the 3D model surface could be undertaken in a number of different ways, the most appropriate of which will depend upon the portion of the patient 20 being treated.

Thus for example in the case of a patient 20 being treated where the irradiated portion of the patient 20 is substantially static and rigid (e.g. a patient with a brain tumour where radiation is applied to a patient's skull), the difference images could be utilised to texture render the computer model of a patient's skull where texture render values correspond to the sum of pixel values for a batch of difference images. That is to say the difference images for a period of time could be added together so as to obtain an image where pixel values correspond to the total detected levels of Cherenkov radiation over that period of time.

Such a texture rendered image could be compared with a model of an expected pattern of Cherenkov radiation based on the expected irradiation in accordance with a treatment plan. If the detected pattern of emitted Cherenkov radiation did not substantially correspond with the expected pattern, that could indicate that the set-up of the treatment apparatus 16 may be incorrect and treatment might be halted and the set up corrected.

Other alternatives may be more appropriate for other portions of the body. Thus for example, in the case of breast cancer and cancers in the thoracic cavity (e.g. lung cancer), merely summing the difference images to obtain a representation of the pattern of irradiation over time may be insufficient. This is because in contrast to the skull, the position of the surface of a patient's chest will vary during the course of a breathing cycle. Although a patient may attempt to hold their chest in a particular position or the breathing of a patient may be monitored and radiation may be applied at approximately the same point in the breathing cycle, this motion may mean that it is necessary to take such movement into account.

This can be achieved in the described system by utilising the 3D models of the surface of a patient which are generated in the course of monitoring a patient. Thus for example, in an embodiment of the present invention, rather than simply texture rendering a single model of the surface of a patient using an accumulated set of difference images for a period of time, the generated models of the surface of a patient could be utilised to divide a set of difference images into sets of images when a monitored surface is in a particular location. Accumulated emission data for the surface when the surface is in particular positions could then be determined. Total emissions from the modelled surface might then be determined by considering the manner in which the modelled surface moves in the course of treatment and hence how the portions of the surfaces captured at different times correspond.

Either of the above two approaches could be utilised to generate a representation of the surface of a patient and the total amount of Cherenkov radiation emitted from that portion of the patient. If the nature and form of the radiation applied to a patient is constant, it would be expected that the total amount of emitted Cherenkov radiation for a given amount of radiation exposure would be substantially constant and hence such a representation of detected Cherenkov radiation would provide an indication of the skin surface radiation dosage.

To the extent that detected Cherenkov radiation does not correspond to skin dosage, differences between the two could be modelled so that an accumulated representation of detected Cherenkov radiation could be converted into data representing skin dosage.

Thus for example, one of the factors which will impact the appearance of Cherenkov radiation emitted from a patient will be the extent to which Cherenkov radiation is emitted by chromophores present in the skin which varies, amongst other reasons, but notably, according to skin tone. The two chromophores which are of greatest significance are blood and melanin, with melanin essentially determining skin tone. Increased concentrations of chromophores in the skin results in lower emission of Cherenkov radiation. The concentration of melanin in the skin increases from white skin tones through to black skin tones. Preferably any estimates of patient radiation dosage based on Cherenkov radiation emissions are corrected to take into account the concentration of chromophores in the patient's skin, in particular, the patient's skin tone, thereby ensuring the estimate of radiation dosage is correct, and not too high or too low. The treatment apparatus can then apply the correct level of radiation to the patient. It will be appreciated that for patients with darker skin tones, the level of Cherenkov radiation emitted will be less than that for a patient with a lighter skin tone, i.e. the estimate of the radiation dosage of the darker skinned patient will be lower than for the lighter skinned patient even though both patients have received the same dosage.

The correction factor can be determined in several ways.

One method relies on comparing the visual appearance of the patient's skin tone and comparing it with a reference set of skin tones. This comparison could be done manually, or utilising images of the patient obtained by the stereoscopic camera to match the tone or colour of the skin as close as possible with a particular tone in the reference set such as the Fitzpatrick and von Luschan reference sets of visual representations of the skin tone as set out in the table below.

| Fitzpatrick type | von Luschan scale | Description |
|---|---|---|
| I | 1-5 | Very light or white, typically Celtic origin, Northern Europe |
| II | 6-10 | Light or light-skinned European, typically Caucasian |
| III | 11-15 | Light intermediate, or dark-skinned European, typically Southern European |
| IV | 16-21 | Dark intermediate or olive skin, typically middle Eastern |
| V | 22-28 | Dark or brown type, typically Asian |
| VI | 29-36 | Very dark or black type, typically African, Caribbean |

An alternative method utilises the stereoscopic camera to monitor images of the surface of a patient, the images then being processed to determine concentrations of blood and melanin and skin collagen thickness. Suitable approaches might be those such as are disclosed in US2008319283 and US2009080726 both of which are hereby incorporated by reference. Briefly, one method describes illuminating the patient with light of a first and second wavelength, receiving the light of the first and second wavelengths after it has been emitted by the patient at a photoreceptor, and analysing the light received at the photoreceptor to provide a ratio between the amount of light remitted of the first wavelength and the amount of light emitted of the second wavelength. This ratio can then be compared to a mathematical model which equates the ratio to a particular characteristic of the skin, for example, the concentration of melanin in the skin. The effects of surface reflection can be eliminated by providing a pair of cross-polarised linear polarizing filters, the first of these is placed in front of the source of illumination and the second in front of the image capture system. There are however other methods which will be apparent to the skilled person which could be used to eliminate surface reflection effects. A colour digital camera can be used as the photoreceptor, although a monochrome digital camera arranged to take sequential images with different coloured light sources could also be used. Both these embodiments may have millions of image pixels or very few pixels, or even just one pixel in the case of the monochrome system. The optical system may work in the visual spectrum, or over an extended spectrum to include non-visible wavelengths. It will be appreciated that the spectroscopic camera used to obtain images of the patient and the treatment apparatus could also be used to capture images of the patient for the purposes of determining the chromophores concentration in the skin.

It will be appreciated that the skin tone can vary according to the portion of the patient being treated, and therefore different skin tones, and therefore correction factors can be applied to the same patient according to the portion of the patient being treated.

The determined concentration of chromophores can then be utilised to convert data of detected levels of Cherenkov radiation into data representative of skin dosage. A further possibility would be to utilise the record of detected Cherenkov radiation emitted from portions of the surface of a patient to infer estimates of internal radiation dosage.

To determine such an estimate, a model of the manner in which radiation is absorbed by tissue would be required. In the case of a relatively homogenous portion of the body, such as the breast, a reasonable approximation would be that radiation is absorbed uniformly. In such circumstance estimates of actual radiation dosage can be determined based upon an estimate of the radiation received by the skin, an estimate of the rate at which the tissue in question absorbs radiation and information about the orientation of the radiation beam. In some embodiments the orientation of the beam could be inferred from the treatment plan. Alternatively, the orientation of a radiation beam which causes Cherenkov radiation to be emitted is determined by processing the images of the treatment apparatus captured by the stereoscopic camera as described above.

One approach to processing data recording the emission of Cherenkov radiation by a surface of a patient would be to process the measured level of Cherenkov radiation data to convert it into an estimate of radiation skin dose. The level of skin dose could then be projected through a model of the tissue based on obtained or inferred data of the orientation of the radiation beam with the level of radiation dose being reduced in accordance with the modelled absorption characteristics of the tissue in question. This processing could be undertaken for each batch of images corresponding to a particular application of radiation and the cumulative radiation dose for the treatment could then be determined. Such a cumulative radiation dose could then be compared with expected dosages based on an original treatment plan.

Where radiation is applied to a less homogenous portion of the body, it will be appreciated that a more complex model of tissues within the patient will be required. One possible approach would be to obtain a CT scan of a patient to identify the location and arrangement of tissues in an area being modelled. The radiation adsorption characteristics of those tissues in the detected 3D arrangement could then be utilised in order to determine estimates of radiation actually received in a similar way to as has been described above.

It will be appreciated that by taking into account the chromophore concentration in the patient's skin, the radiation dosage can be corrected such the correct level of radiation is applied to the patient, regardless of skin tone.

When positioning a patient for radio therapy treatment, it is important that a patient is accurately positioned relative to the treatment iso-center. For that reason it is very important that any radiation dosage monitoring system is accurately calibrated so as to be able to identify the relative position of a patient relative to the treatment iso-center.

The conventional approach to identifying the location of a treatment iso-center was 20 introduced by Lutz, Winston and Maleki at Harvard Medical School in 1988 which is described in Lutz W, Winston K R, Maleki N. A system for stereotactic radiosurgery with a linear accelerator. Int J Radiat Oncol Biol Phys. 1988; 14(2): 373-81. In the Winston-Lutz system initially, the estimated location of the iso-center is highlighted utilizing a set of laser beams arranged to intersect at a point corresponding to the 25 expected location of the iso-center. A calibration phantom comprising a small metallic ball made of steel, titanium or tungsten is then fixed on the treatment table by a locking mechanism. The phantom position is adjustable in three directions by means of a micrometer tool. The collimator used for radiotherapy is attached to the gantry head and the ball is placed as closely as possible to the estimated position of the iso-center 30 by aligning the marks on the phantom with the treatment room lasers. The collimated beam is used to expose a radiographic test film mounted perpendicular to the beam direction on a stand behind the ball. Differences between the center of the sphere shadow and the field center identifies the differences between the true iso-center and the iso-center as indicated by the treatment room lasers. The offset is read on each film using transparent template guidance scales or scanning the film and software analysis. Knowing this offset, the treatment room lasers highlighting the estimated iso-center location can be utilized to locate a calibration object such as a cube of known size with markings on its exterior. The calibration object is then imaged by the stereoscopic camera 10 and the combination of the knowledge of the offset of the point highlighted by the room lasers and the known size of the calibration object enables the stereoscopic camera to be calibrated to relate distances in images to real world distances and to relate those distances to the location of the treatment iso-center.

One of the primary disadvantages of the above described method of calibrating a stereoscopic camera relative to the identified position of the iso-center in the manner described is that it is reliant upon the accuracy with which room lasers identify and continue to identify a fixed point. For this reason it is necessary to re-calibrate the system periodically to ensure that the identified location has not changed. Even then, the accuracy with which the camera system is calibrated remains dependent upon the accuracy with which the calibration object is positioned and the accuracy of the room lasers.

However, in the above described radiation dosage monitoring system an alternative approach could be utilized to confirm the accuracy of the camera calibration since 20 images of a calibration object could be obtained and patterns of induced Cherenkov radiation appearing on the surface of the calibration object could be recorded. The recorded patterns of induced Cherenkov radiation could then be utilized to confirm that the stereoscopic camera system correctly identified the location of the treatment iso-center. This could be achieved by irradiating the calibration object from two or more 25 different orientations and utilizing the detected patterns of induced Cherenkov radiation and the identification of the orientation of the radiation beam to identify a point in space where the radiation beams applied with the apparatus in different orientations converge. If the stereoscopic camera is accurately calibrated this should correspond to the treatment room iso-center in the co-ordinate system of the computer models generated by the stereoscopic camera.

Such a verification process would be relatively easy to undertake and would be independent of any errors which arise due to the misidentification of the treatment room iso-center by room lasers. When undertaking such a calibration of the camera system, the calibration object could be selected so as to assist with the creation of an identifiable record of the path of the radiation beam. Thus for example the calibration object might be made of or coated with a fluorescent or scintillating substance which enhances the output of detectable light induced by Cherenkov radiation. Although in the above described embodiment a radiation dosage monitoring system has been described in which a single stereoscopic camera 10 is utilised to obtain images of a patient 20, it will be appreciated that in other embodiments multiple cameras could be utilised. In such systems images of Cherenkov radiation from a number of different viewpoints could be utilised to determine estimates of total emissions. Given the relativity low level of emitted Cherenkov radiation having multiple image detectors may increase the sensitivity of the monitoring system.

In such a system, images of a patient from different cameras could be utilised to generate a single model of the surface of a patient and images of the surface and detected emissions of Cherenkov radiation obtained by the different cameras could then be utilised to texture render the surface so as to generate a representation of the emissions. As with the previous embodiments, the texture render data could be based on images corresponding to a short period of time and the detected pattern of Cherenkov radiation could be compared with an expected or estimated pattern for that portion of the treatment plan. Alternatively, cumulative radiation for an extended period of time could be determined and displayed.

In the above embodiments various references have been made to the detection of emissions of Cherenkov radiation and utilising the emissions to generate a texture rendered representation of a surface model of a patient. It will be appreciated that when a 3D wire mesh model of a surface of a patient is available, and images of emissions or expected patterns of emissions of Cherenkov radiation from one or more viewpoints are available, it is possible to generate representations of the appearance of detected patterns of emissions (or estimated patterns of emissions) from other viewpoints using conventional texturing rendering techniques. This potentially simplifies the comparison between actual detected emissions and an expected pattern of emissions. Thus for example in some embodiments of the present invention, the expected pattern of Cherenkov radiation for a particular treatment might be determined for a viewpoint corresponding to the actual viewpoint of one or more cameras. A difference image could then be determined and the difference between the expected pattern and the actual obtained images could be displayed to provide feedback which might indicate positioning or treatment errors.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program. For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A radiation dosage monitoring system comprising:
   a processing module; and
   a 3D camera operable to obtain images of a patient undergoing radiation treatment;
   the 3D camera comprising:
      a first type imaging sensor configured to record images of the patient, such images being provided to said processing module, which is configured to process the images of the patient to generate a 3d model of a surface of the patient; and
      a second type imaging sensor configured to capture Cherenkov images of Cherenkov radiation emitted from the surface of the patient when the patient is irradiated by a radiation beam,
   wherein the Cherenkov images represent detected Cherenkov radiation and any subsequent secondary and scattered radiation originating due the initial Cherenkov radiation emitted from the surface of the patient when the patient is irradiated by the radiation beam;
   wherein said processing module is configured to process images obtained by the 3D camera utilizing data indicative of chromophores present in the patient's skin to apply a correction factor to such images to account for absorption of Cherenkov radiation by chromophores in the skin when utilizing the images to generate a representation of radiation applied to the surface of the patient; and
   wherein said processing module is further configured to generate a representation of radiation dosage received by the patient's skin by texture rendering data representative of the radiation dosage received by the modelled portion of the surface of the patient undergoing radiation treatment onto the generated 3D model.

2. A radiation dosage monitoring system according to claim 1 wherein the processing module is operable to process images by:
   obtaining a first image of a patient from a viewpoint without radiation being applied to the patient;
   obtaining a second image of a patient from the same viewpoint under the same lighting conditions as the first image with radiation being applied to the patient; and
   determining a difference image subtracting image values for pixels in the first image from corresponding pixel values in the second image.

3. A radiation dosage monitoring system according to claim 2 wherein the processing module is operable to process images by determining the sum of pixel values in difference images for corresponding pixels in a set of images of a patient in the same position from the same viewpoint under the same lighting conditions as the first image with radiation being applied to the patient.

4. A radiation dosage monitoring system according to claim 3 wherein the processing module is operable to process images to identify saturated pixels or pixel values corresponding to statistical outliers appearing in images which do not appear in a successive image; wherein such saturated pixel values are not utilised to determine a representation of the location of the portions of a patient irradiated by radiation resulting in the emission of the Cherenkov radiation.

5. A radiation dosage monitoring system according to claim 3 wherein said processing module is operable to convert said processed images into images representative of radiation skin dosage by modifying pixel values in accordance with a correction factor to account of the absorption of Cherenkov radiation and any subsequent secondary and scattered radiation originating due the initial Cherenkov radiation by chromophores present in a patient's skin.

6. A radiation dosage monitoring system according to claim 5 wherein the processing module is operable to process images obtained by the 3D camera to determine data indicative of chromophores present in a patient's skin and the correction factor applied is determined on the basis of said data.

7. A radiation dosage monitoring system according to claim 6 wherein the data indicative of chromophores present in a patient's skin comprises a visual estimation of the skin colour of the patient based on a comparison with a reference set of skin tones and the correction factor applied is determined on the basis of said data.

8. A radiation dosage monitoring system according to claim 1 wherein the processing module is operable to determine representations of the radiation dosages received by a patient's skin when the surface of the patient is in each of a plurality of different positions to identify corresponding portions of the patient's skin in the different positions and utilise those plurality of representations to determine a representation of the total radiation dosage received by a patient's skin.

9. A radiation dosage monitoring system according to claim 1 wherein the 3D camera comprises a plurality of image detectors and the processing module is operable to determine estimations of radiation applied to the surface of a patient utilising images obtained by the plurality of image detectors to texture render the generated 3D model of the surface of a portion of a patient undergoing radiation treatment.

10. A radiotherapy treatment system comprising a treatment apparatus operable to irradiate a patient with radiation; and
    a radiation dosage monitoring system according to claim 1 wherein the treatment apparatus is operable to inhibit the irradiation of a patient if the estimations of radiation dosages received by the modelled portion of the surface of the patient determined by the radiation dosage monitoring system differ from a predetermined estimations of radiation dosages of a patient irradiated in accordance with a defined treatment plan by more than a threshold amount.

* * * * *